(12) United States Patent
Bureau et al.

(10) Patent No.: US 10,583,026 B2
(45) Date of Patent: Mar. 10, 2020

(54) FITTING ELEMENT WITH CONTROLLED STIFFNESS

(75) Inventors: Maxime Bureau, San Sebastián (ES); Je Hyung Jung, San Sebastián (ES); Thierry Keller, San Sebastián (ES)

(73) Assignee: Fundacion Tecnalia Research & Innovation, Donostia-San Sebastian (ES)

( * ) Notice: Subject to any disclaimer, the term of this patent is extended or adjusted under 35 U.S.C. 154(b) by 701 days.

(21) Appl. No.: 13/520,102

(22) PCT Filed: Dec. 30, 2009

(86) PCT No.: PCT/EP2009/068020
§ 371 (c)(1),
(2), (4) Date: Aug. 9, 2012

(87) PCT Pub. No.: WO2011/079865
PCT Pub. Date: Jul. 7, 2011

(65) Prior Publication Data
US 2012/0310126 A1    Dec. 6, 2012

(51) Int. Cl.
*A61F 5/01* (2006.01)
*A61F 5/058* (2006.01)

(52) U.S. Cl.
CPC ........ *A61F 5/0104* (2013.01); *A61F 5/05833* (2013.01)

(58) Field of Classification Search
CPC ........ A61F 5/05; A61F 5/058; A61F 5/05816; A61F 5/05833; A61F 5/05825; A61F 5/05841; A61F 5/05858; A61F 2007/0024; A61F 2007/0018; A61F 2007/0041; A61F 2007/0042; A61F 2007/0043; A61F 2007/0029; A61F 2007/0031;
(Continued)

(56) References Cited

U.S. PATENT DOCUMENTS 3,701,349 A * 10/1972 Larson ................ A61F 5/05816
602/13
3,745,998 A    7/1973 Rose
(Continued)

FOREIGN PATENT DOCUMENTS

EP    0 267 640 A1    5/1988
WO    WO 2004/082544 A1    9/2004

OTHER PUBLICATIONS

European Patent Application No. EP 1 319 377 A1 (Kohlbrat and Bunz GMBH [AT]), published Jun. 18, 2008 (abstract).
(Continued)

*Primary Examiner* — Anna K Kinsaul
*Assistant Examiner* — Camtu T Nguyen
(74) *Attorney, Agent, or Firm* — Florek & Endres PLLC

(57) ABSTRACT

The invention refers to a body fitting element with negative pressure controlled stiffness comprised of a gas tight envelope (1), a plurality of layers fitted in the envelope (3) and a valve (2) adapted to evacuate the interior of the envelope, characterized in that the layers comprise a core (4a) made of a material with a high Young's modulus and flexibility and a first cover layer at both sides of the core made of a material with high friction coefficient (4b). Orthoses and protective equipments fabricated with the fitting element can be shaped and fitted to the body in an optimal manner.

11 Claims, 7 Drawing Sheets

(58) Field of Classification Search
CPC ........... A61F 2007/0034; A61F 5/0104; A61B 2017/00561; A61B 2017/00566; A61M 1/0049; A61M 1/00
USPC ............................................ 602/5, 6, 13, 14
See application file for complete search history.

(56) References Cited

U.S. PATENT DOCUMENTS

| | | | | |
|---|---|---|---|---|
| 4,549,537 | A * | 10/1985 | Ender | A61F 5/05866 602/21 |
| 4,848,364 | A * | 7/1989 | Bosman | A61F 2/0063 128/849 |
| 4,862,879 | A | 9/1989 | Coombs | |
| 5,906,577 | A * | 5/1999 | Beane | A61B 17/0293 600/206 |
| 5,948,707 | A * | 9/1999 | Crawley | A41D 31/02 428/422 |
| 6,066,107 | A | 5/2000 | Habermeyer | |
| 6,251,065 | B1 | 6/2001 | Kochamba et al. | |
| 6,796,940 | B2 * | 9/2004 | Bonadio | A61B 17/02 128/850 |
| 7,037,283 | B2 * | 5/2006 | Karason et al. | 602/6 |
| 2003/0139694 | A1 * | 7/2003 | Rugfelt | A61F 5/055 602/12 |
| 2004/0082891 | A1 | 4/2004 | Daugherty et al. | |
| 2004/0138762 | A1 * | 7/2004 | Therin | A61F 2/0063 623/23.75 |
| 2005/0137513 | A1 | 6/2005 | Rugfelt | |
| 2008/0319362 | A1 * | 12/2008 | Joseph | A61F 5/01 602/7 |
| 2009/0234309 | A1 * | 9/2009 | Vitaris | A61M 1/0049 604/313 |
| 2012/0302931 | A1 * | 11/2012 | Yu | 602/6 |

OTHER PUBLICATIONS

PCT International Application No. WO 03/047961 A2, (Siemens, AG [DE]), published Jun. 12, 2003 (abstract).
International Search Report issued by the International Searching Authority (ISA/O.E.P.M.) dated Sep. 3, 2010 in connection with International Application No. PCT/ES2009/070643.

* cited by examiner

FITTING ELEMENT WITH CONTROLLED STIFFNESS

This application is a § 371 national stage application of PCT International Application No. PCT/ES2009/070529, filed Nov. 25, 2009, the contents of all of which are hereby incorporated by reference into this application.

FIELD OF THE INVENTION

The present invention applies to medical devices such as casts, functional orthoses, insoles, and emergency medical devices such as splints for limbs and full body first aiders. In addition, the present invention is capable of being incorporated into sporting goods like skates, ski boots, and protective equipments in sports such as knee and chest guards. In particular, the invention relates to a fitting element with variable stiffness controlled through negative pressure, such as suction or vacuum.

STATE OF THE ART

For many years, several kinds of orthopedic devices have been employed in many situations. One of them is the orthopedic cast, made of heavy, bulky, awkward material such as wrapping or gauze bandage. A functional orthosis (brace) is worn by patients after surgery for treatment of injury to a joint or ligament and is not as rigid as a cast. The orthosis is a conservative treatment serving two purposes: first, stabilization of the joint in order to control its movement and second, joint angle limitation in an adjustable and controllable manner to prevent recurrence of injury to the joint.

These orthopedic devices have rigid properties in order to provide support and stabilization of affected body parts. Rigidity, however, brings on several disadvantages. For example, conventional plaster casts are time consuming and awkward to fabricate in order to provide rigidity. Moreover, because of the varieties of shapes and proportions of human body and its limbs, preformed casts have generally been unsatisfactory except for small, relatively uniform portions of the body such as the neck. Having once been formed, they are generally not removed until conclusion of the period of treatment. These enclosures are objectionable from many standpoints including cleanliness and ventilation of the closed tissue. In addition, rigid parts of splints and orthoses make difficult for these devices to be positioned correctly on human body and affected limbs.

This difficulty is easily found in protective equipments in sports, for example, knee and chest guards, and helmets because they also have rigid parts to safeguard body parts against external impacts when failing down or crashing.

Orthopedic devices and protective equipments for the body and its parts are highly useful if they are light in weight and capable of quick and convenient conversion from the soft state in which they are easily formed and shaped to conform to the human body and affected limbs, to the rigid state in which they provide support and stabilization.

Use of negative pressure such as suction or vacuum provides a simple way to implement quick and convenient conversion from the soft state to the rigid state and vice versa. The basic structure of devices employing negative pressure comprises inner fillers which are commonly movable particles and a flexible, air-impermeable thin outer cover. The structure normally enables the device to be easily and readily fitted around the body and affected limbs. When the device becomes the desired shape in the desired position, it is subjected to negative pressure and then atmospheric pressure compresses the flexible outer cover and applies substantial pressure to the entire mass of particles. The frictional force between the particles and the cover resist movement relative to each other, thereby providing rigidity. Usually a valve is included for sealing the cover when evacuated to maintain rigidity of the device. The soft state from the rigid state is obtained easily and quickly by opening the valve and whiff.

Several patents about orthopedic devices employing negative pressure have been published. In addition, some patents show the method to implement a custom-shaped and easily-remolded seat and back cushions for furniture and vehicles by means of negative pressure. For example, Pat. U.S. Pat. No. 3,745,998, issued Jul. 17, 1973, describes a vacuum formed support structures and immobilizer device in which foamed "micro-balloon" polymer article is used as the inner filler. The invention of this patent shows versatile applications such as limb immobilizers, lightweight sling-act and so on.

Pat. U.S. Pat. No. 4,862,879, published Sep. 5, 1989, discloses orthopedic splints comprising a plurality of self-contained compartments having flexible impermeable walls, each compartment containing fluent granular material and being provided with a valve allowing evacuation and inflation respectively to rigid and soft mode.

Pat. U.S. Pat. No. 6,066,107, published May 23, 2000, describes an apparatus for the fixation of the extremities in a surrounding manner comprising a double walled cuff-forming cushion and outer plastic sleeve. The cuff-forming cushion can be formed into a sleeve and is made vacuum-tight with a plurality of filling bodies and outer plastic sleeve acts as a buffer against blows during impact loads and provide resistance during walking.

Pat. U.S. Pat. No. 6,251,065, published Jun. 26, 2001, describes a tissue stabilizer comprising a flexible rigidifying bladder. This rigidifying bladder includes opposing layers of mesh between which a plurality of movable beads are disposed. The rigidifying bladder may include a plurality walls which divide the inner chamber into a plurality of cells or separate the chamber into layers. This invention is configured for many medical applications such as portable neck brace, splint for stabilizing, particularly useful in stabilizing the heart during cardiac procedures.

Pat. U.S. 2004/0082891, issued Apr. 29, 2004, discloses a vacuum splint device comprising a sleeve, a plurality of substantially T-shaped straps and an intake/exhaust valve tube assembly. The sleeve preferably houses a plurality of particles.

The main disadvantage of the use of particles or balls (beads) as inner filler is difficult to distribute the particles satisfactorily when the cover is situated in a non-horizontal plane such as human body and limbs. Some patents show the solution to avoid the disadvantage of particles or ball filler.

Pat. U.S. 2005/0137513, published Jun. 23, 2005, discloses a structure to maintain an homogeneous thickness for devices for supporting and stabilizing an injured person or body parts. The device has an inner region enveloped by two flexible films and the inner region is divided into two insertion bodies which are respectively formed with two air-permeable, flexible material strips. Each insertion body is divided into chambers containing loose particles, by way of intersecting seams formed between the material strips. The seams on both insertion bodies are staggered in relation to each other in both directions in such a way that the particles combine to form a substantially homogeneously thick particle layer.

Pat. EP 267,640 (A1), published May 18, 1988, describes a covering sheet for surgical use which doesn't allow the granules to accumulate at one side of the covering by means of non-woven fabric.

As the aforementioned two patents use extra chambers containing particles or mechanical matrices consisting of ball and bar, they require additional space. Therefore, the thickness of the devices inevitably increases.

SUMMARY OF THE INVENTION

The present invention relates to a fitting element in accordance with claim 1 that can be readily formed and shaped to conform to any member, portion or extremity of the user's body, so that medical, emergency medical and protective devices which are made up of the elements of the Invention provide minimum resistance to movement and their shaping. The body fitting element with negative pressure controlled stiffness comprises a gas tight envelope, a plurality of layers fitted in the envelope and a valve adapted to evacuate the interior of the envelope, and the layers comprise a core made of a material with a high Young's modulus and flexibility and a first cover layer at both sides of the core made of a material with a high friction coefficient. The invention is also related to different orthoses comprising one or more of these fitting elements and other layers for adapting the apparel to the body and achieving optimal rigidity. Further aspects of other embodiments can be found in the dependent claims.

Advantages and applications of the present invention will become apparent in the following detailed description, claims and drawings.

BRIEF DESCRIPTION OF THE DRAWINGS

To complete the description and in order to provide for a better understanding of the invention, a set of drawings is provided. Said drawings form an integral part of the description and illustrate preferred embodiments of the invention, which should not be interpreted as restricting the scope of the invention, but just as examples of how the invention can be embodied. The drawings comprise the following figures.

DETAILED DESCRIPTION OF THE INVENTION

Figure 1:
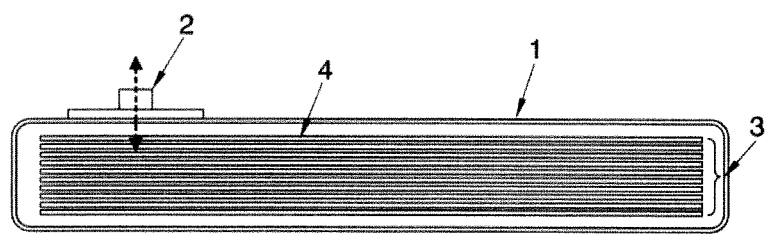
FIG. 1 shows a sectional view of a fitting element according to the invention.

In a first aspect of the invention shown in FIG. 1, the fitting element comprises a laminate of several flexible layers (3) inserted into an hermetic stretchable envelope (1) that is suitable for being subjected to a controlled pressure.

When a vacuum is applied, the layers are compressed together increasing the friction between them, which in turn increases the stiffness of the stratified material. The structure therefore has variable state possibilities, from soft at atmospheric pressure to rigid when depressurized.

The novelty of this design is in the structure and materials of the layers (4), that allow the customization of orthopedic devices capable of conforming to the individual shape of the limb of the patient. The soft state permits to shape the limb and the rigid state permits to lock it to provide support and stabilization.

To that purpose, an important issue is to have a high stiffness ratio between the soft and hard states.

Figure 2:
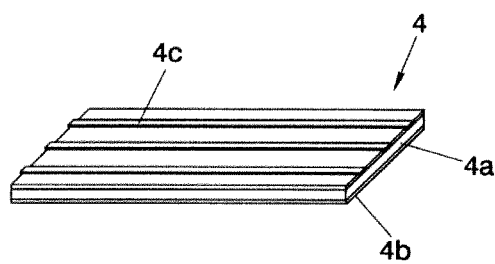
FIG. 2 is a perspective view of one of the layers inside the fitting element.

To obtain the desired property of the layer in each mode, the layer (4) comprises, in a preferred embodiment shown in FIG. 2, 3 different materials in series. The layers (4) comprise a core layer of high Young's modulus, flexible, high tensile stress at the rupture and thin first material (4a), for example, Dacron® a textile made of polyethylene terephthalate (PET) fibres as the "140 TNF MT" from "dimension Polyant" which has a traction Young's modulus of 2 GPa for a thickness of 200 µm, coated on both sides with a first cover layer of thin high friction coefficient material (4b), for example, 10 µm of polyurethane (PU). As a second layer, straps of, for example, Teflon© (4c) are stuck onto one side of the second material (4b). Other materials and coatings other than Teflon© in the form of strips or straps are suitable, provided they have a low friction coefficient.

Figure 3:
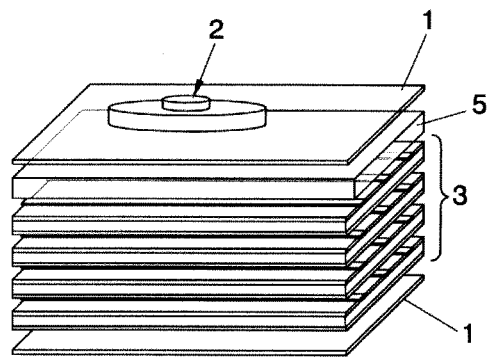
FIG. 3 is a perspective view of the fitting element according to the invention.

As shown in FIG. 3, a side of the layer onto which Teflon© is applied contacts a side of the next layer having only the second material with high friction coefficient. When a negative pressure is applied, the laminated sheets (4) are compressed together and deformed, so that the high friction coefficient surfaces (4b) of the first layer are in contact with one another and the stiffness is high.

Figure 8:
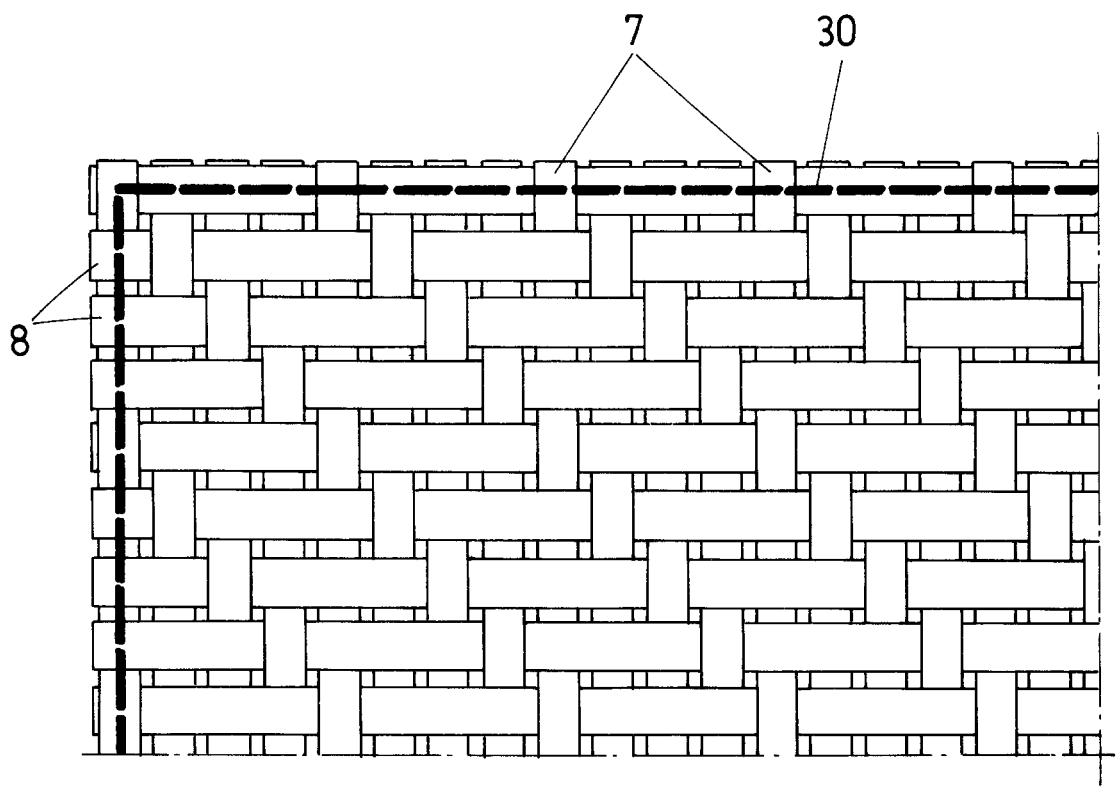
FIG. 8 is a partial top view of sewing lines according to another embodiment.

When atmospheric pressure is inside the envelope, the layers are uncompressed and only the low friction straps (4c) are in contact with the nearest layer (4). The low friction material (4c) can be made compressible, helping to separate the layers following the removal of the vacuum and thereby allowing rapid separation of the layers (4) of the laminate (3). As shown in FIG. 8, instead of Teflon®, sewing lines of polyester thread or any other suitable thread can be used, which lowers the cost of the orthosis.

To apply an homogenous force during compression of the laminate, an air permeable layer, for example foam (5) is inserted parallel with the laminate (3) into the flexible envelope (1). The foam layer (5) allows the force of the vacuum to be well distributed. As the foam layer (5) changes its thickness during the vacuum process, it is recommended that the air permeable layer, is placed on the side of the laminate (3) that is not to be fitted, thus avoiding an unwanted gap.

To help prevent formation of wrinkles between the layers (4), the compressive foam (5) is installed in contact with the internal side of the envelope (1) and the first layer of the laminate (3). This applies a continuous, low orthogonal force on the layers (4), flattening the layers (4) thereby evading the formation of wrinkles. The valve (2) is inserted into the envelope (1) on the side next to the foam (5). This avoids the blocking of the airflow by a layer of the laminate sticking to the valve orifice.

Figure 4:
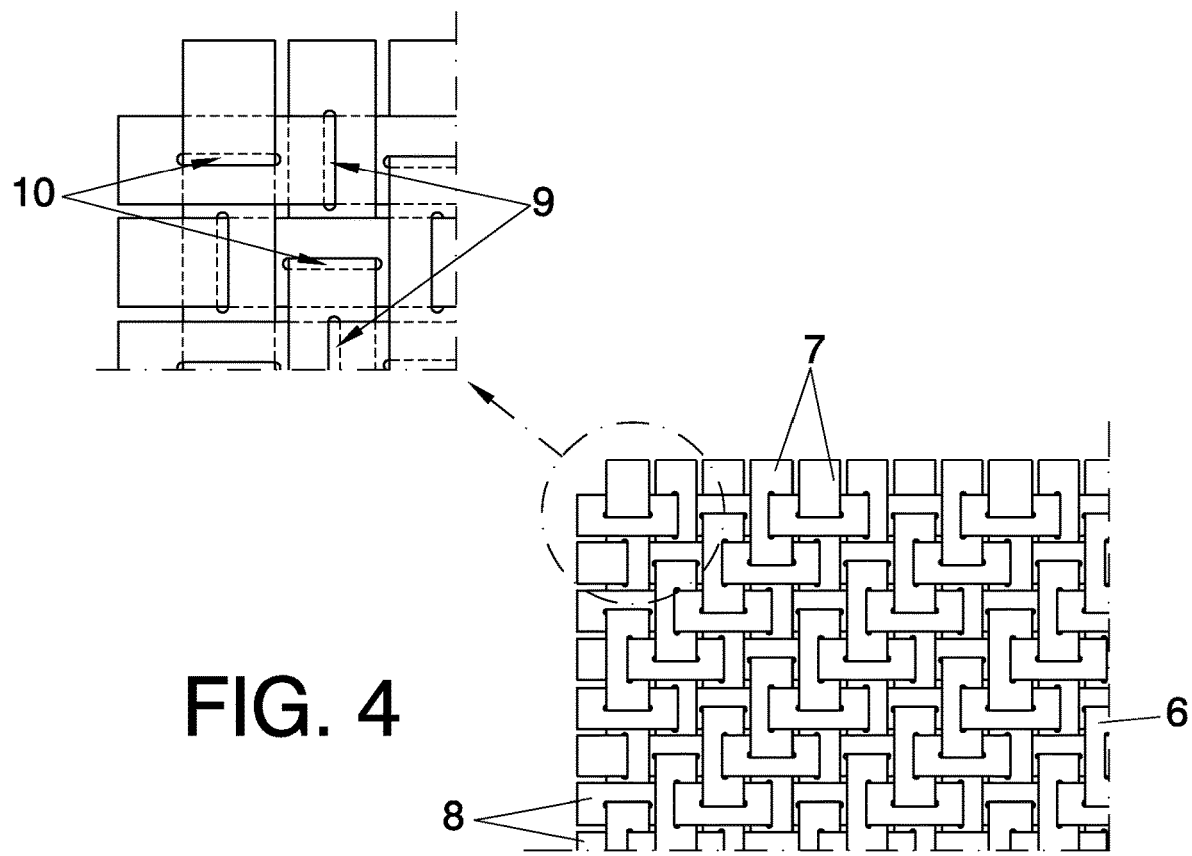
FIG. 4 is a top view of a ribbon weaving structure according to another embodiment.
Figure 5:
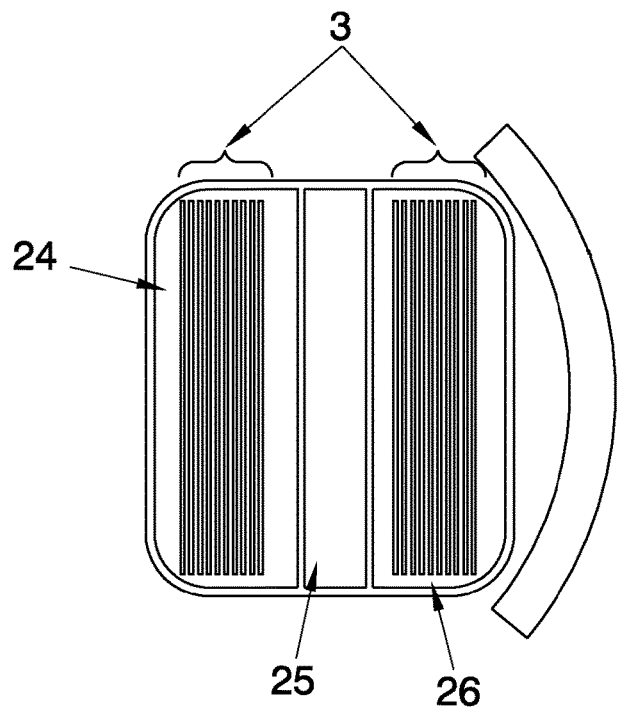
FIG. 5 is a sectional view of the structure for automatic installation according to one embodiment of the invention.

A core material (4 a) with a high Young's modulus is necessary to make a laminate with a high stiffness state; however these materials have a low extensibility. Because they are not extensible they cannot fit all 3D shapes. In order to fit 3D forms, especially the ones with irregular surfaces, the first material with a high Young modulus is provided in the form of ribbon weavings (6), to add degrees of freedom to the fabric, as shown in FIG. 4. To keep this structure organized after many uses and avoid overlaps and loss of the ribbons (7) and (8), the vertical and horizontal translations of the ribbons are limited. These translations are limited by inserting the horizontal ribbons (8) through slits (10) in the vertical ribbons (7) and vertical ribbons (7) through slits (9) in the horizontal ribbons (8). These slits are a little wider than the ribbons to facilitate insertion and allow rotations. Allowing slight rotations between horizontal and vertical ribbons in the plane of the surface is important to permit the structure to change shape.

Due to the high cost of the manufacturing of "stable" ribbon weavings made with slits, a standard ribbon weaving can be used if the borders are sewn. Any 2D pattern can be sewn and cut, taking care to ensure that both ends of each ribbon in the pattern have been sewn.

The material used to make the ribbons (7) and (8) is composed of the flexible high modulus textile (4a) and forms the core, it is then covered on both sides by the high friction coating (4b). In this particular embodiment using the ribbon shaped high Young modulus first layer, there is no need for the low friction strip (4c), because the wave forms created by the weaving allow the separation of the layers once an internal pressure is applied without any external help.

Making the weaving smaller, i.e. with smaller ribbon's width, allows a better fitting. For human body fitting, a 5 mm width of the standard ribbon weaving and a 8 mm width for a slips ribbon weaving (6) gives a good result, but any width can be used depending on the purpose.

The modulus of elasticity in bending ($E_f$) of the fitting element was experimentally obtained by a three point flexural test. A sample used in an experiment was 50 mm in width and 3.5 mm thickness, and was composed of 8 layers of Dacron® "140 TNF MT" from Dimension Polyant and coated by a 10 μm PVC glass in both sides. An experiment was executed with a support span of 500 mm. The results show:
i) the sample under atmospheric pressure is not capable of supporting its own weight,
ii) the sample depressurised at 70% of vacuum support its own weight with 11.75 mm deflection and,
iii) the sample under the same condition to ii) has a deflection of 60.25 mm when 210 gr are loaded.
This laminated sample has an equivalent flexural modulus of an isotropic material of 600 MPa.

The main advantage of the invention is that the fitting element uses no granules or particles, but only textile layers. This allows a thickness of the device employing the fitting element to decrease in comparison with that using granules or particles. The wide contact area between the layers under negative pressure enables the stiffness of fitting element to increase.

Figure 6:
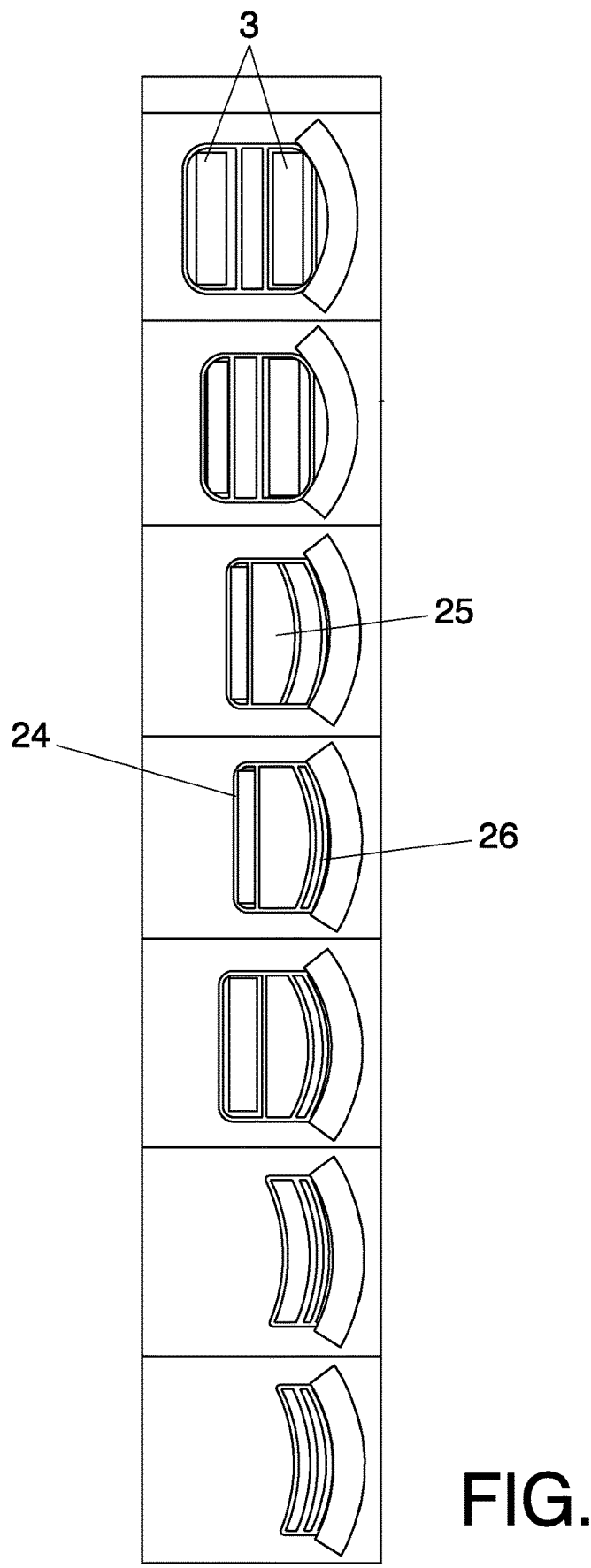
FIG. 6 is a representation of the process of automatic installation.

One challenge is ensuring the orthosis is in close contact with the body at the time of fitting, before the vacuum is applied. A second aspect of the invention provides a method of fitting the orthoses to the body automatically. The structure to be used requires 2 independent chambers (24, 26) with laminate (3) inside separated by an empty chamber (25) as shown in FIG. 6.

The following table describes a possible sequence of steps to automatically position a structure to fit a body part.

| Phase Number | Description | Chamber Pressure A | B | C |
|---|---|---|---|---|
| 1 | The structure is soft, position it by hand around the body part to be fitted | 0 | 0 | 0 |
| 2 | Apply a vacuum in the external chamber (chamber far from the body) to create an external rigid compartment | −1 | 0 | 0 |
| 3 | Inflate the intermediate empty chamber adjacent to the rigid compartment to compress the internal chamber (the closest one to the body)on the body | −1 | 1 | 0 |
| 4 | Apply a vacuum in the internal chamber to rigidify it, thereby creating an internal rigid compartment | −1 | 1 | −1 |
| 5 | Remove vacuum and allow return of atmospheric pressure in the external rigid comportment and intermediate chamber to make the external compartment soft | 0 | 0 | −1 |
| 6 | Apply a vacuum in the intermediate chamber to press the external soft compartment to the internal rigid compartment | 0 | −1 | −1 |
| 7 | Apply a vacuum in the external compartment to rigidify it | −1 | −1 | −1 |

The shape of, for example, a leg changes during the day. Furthermore, the shape of a leg fluctuates in function of muscle activation. The automatic installation of the structure coupled to a real time control permits the orthosis device to fit constantly to the fluctuating shape of the limb.

Figure 10:
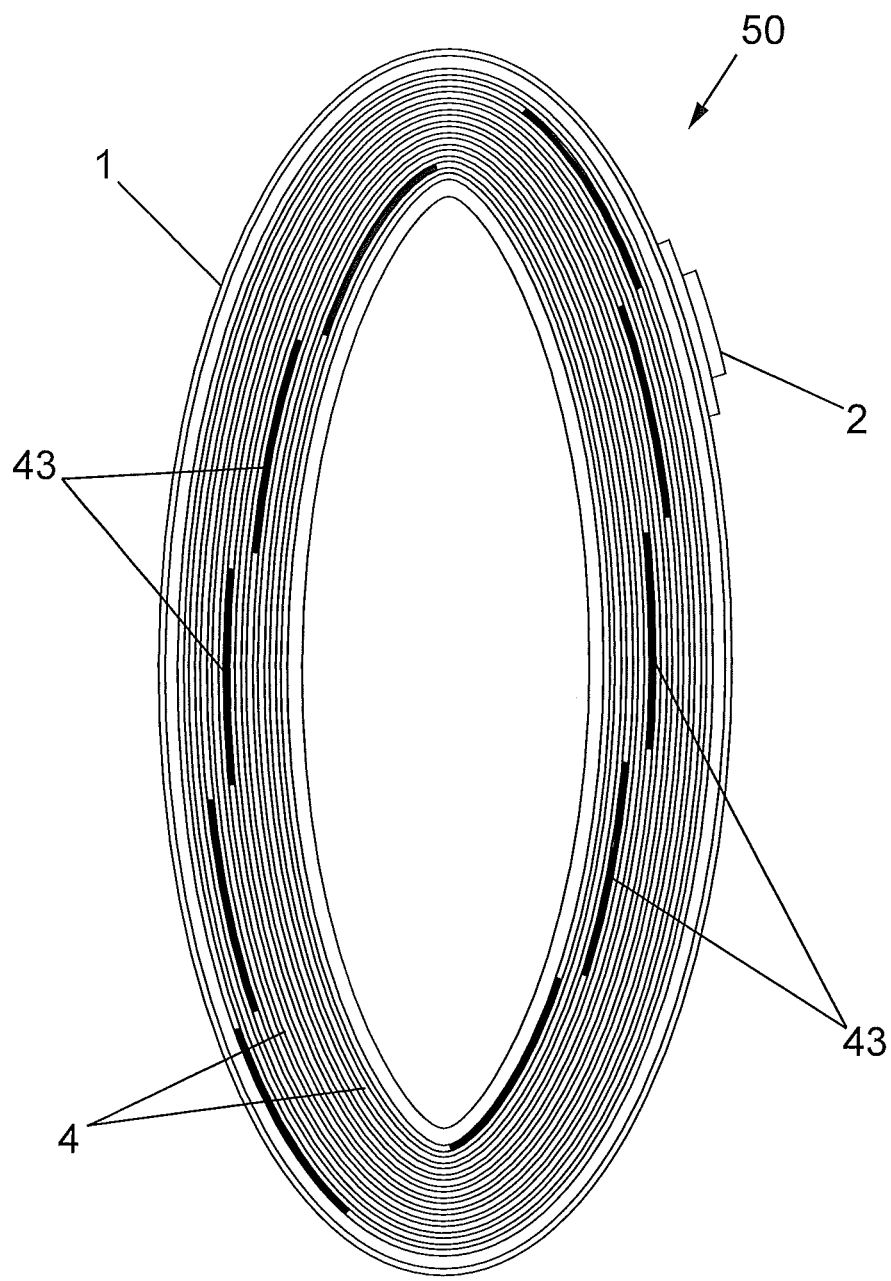
FIG. 10 is a partial top view of sewing lines according to another embodiment.

The present invention can be configured to make functional orthoses, especially knee, neck or elbow orthoses. In a particular embodiment shown in FIG. 10, a collar (50) for the neck is provided. The high modulus material presents a low extensibility and thus, a loop made with this material cannot change its size. This problem is solved by adding, for example by sewing or gluing a stretchable or elastic part (43) into a loop formed by each layer (4). To not weaken the final structure in the elastic part (43), the elastic part (43) of each loop's layer (4) can be installed in a different position to homogeneously distribute the loss of strength in all the structure.

Figure 7:
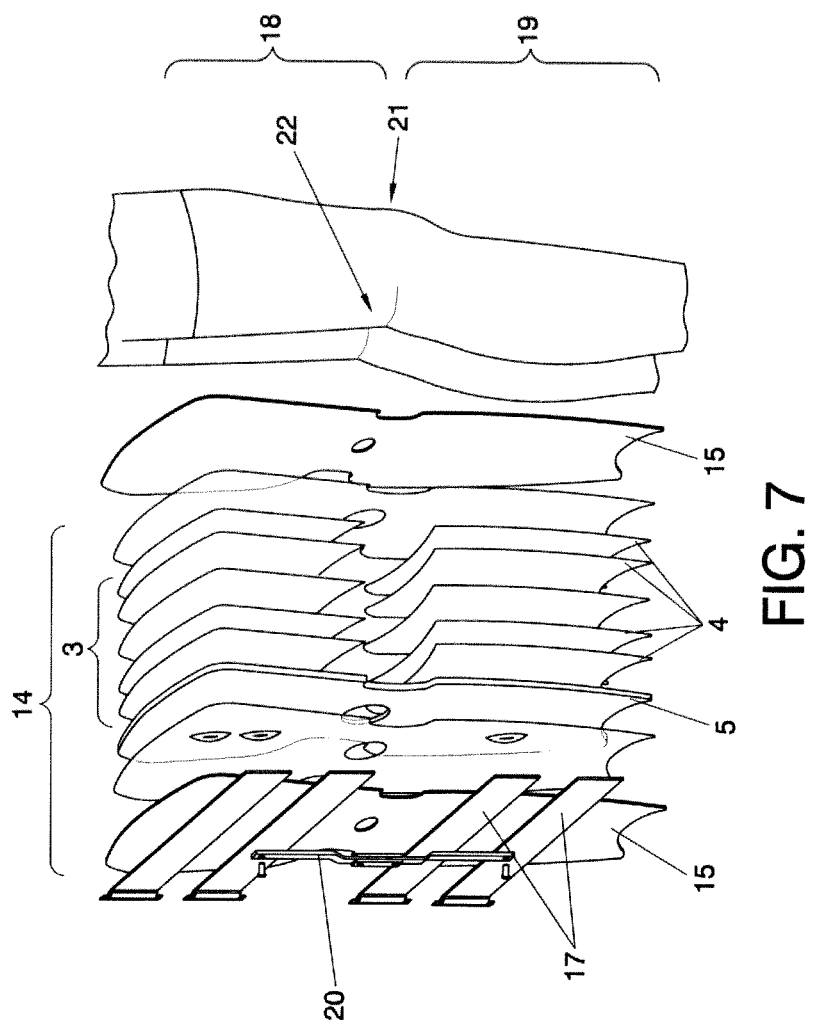
FIG. 7 is an exploded view of a leg orthosis based on the invention.

FIG. 7 shows how to combine the stratified structure of the invention with mechanical connection components to provide support in the knee joint motion. A universal knee brace orthosis (14) based on the invention is constructed with a stretchable external envelope (15) made in neoprene rubber and/or nylon. The device can be produced in different generic sizes, i.e. "small, medium, large". The orthosis is closed with a self-gripping fastener like Velcro© and secured in place by adjustable straps (17). In order to increase the comfort of the othosis, the knee cap (21) and popliteal region (22) remain uncovered.

Two variable stratified stiffness parts (3) are inserted into the external envelope (15), one in the upper leg part (18) and another one in the lower leg part (19). One of the largest problems with knee orthoses is the tendency for the orthosis to "slide" down the leg, resulting in a loss of function. With this design however, the orthosis is tailored to the individual the result being an excellent and close fit to the patient's leg. This is of particular importance around the area under the knee which has a smaller diameter than the calf and can thus serve to prevent "sliding" of the orthosis.

Figure 9:
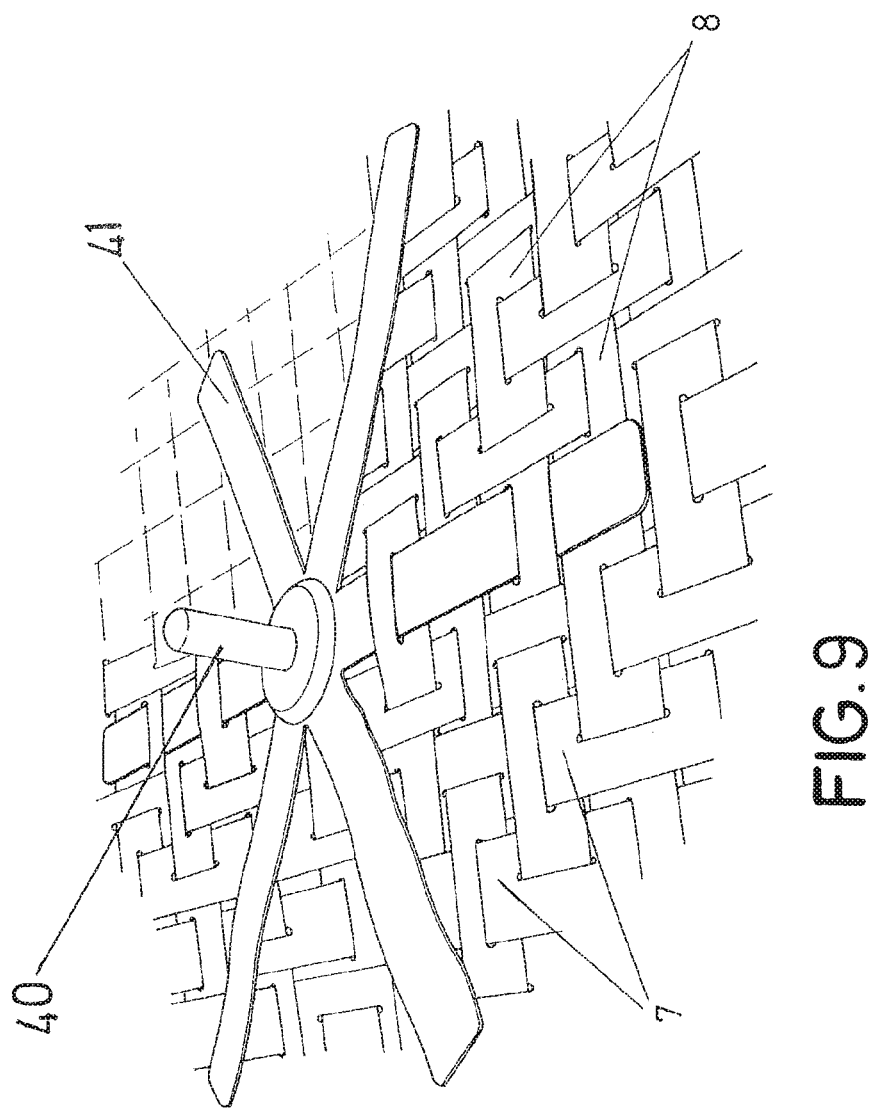
FIG. 9 is a partial perspective view of a thin ramified metal layer with a fixation according another embodiment.

In this design the laminate of textile's layers (3) of the variable stratified stiffness is composed of for example 4 layers of the standard ribbon weaving (6). The valves of the hermetic envelopes are connected to control the pressure at only one point. In order to allow hard fixation of polycentric hinges (20) or other type of protective knee joints, two fixations in the variable stiffness structure are inserted. As shown in FIG. 9, this fixation (40) has a part accessible outside the hermetic envelope, which passes through a valve, and fixes the polycentric hinges and an internal part inserted between the textile's layers (3). In order to allow the fixation (40) to fit several 3D shapes without losing its strength capacity, a thin sheet of metal with a ramified form (41) e.g. a star or flake, is used, whose ramifications are inserted through the slits of the vertical or horizontal ribbons (7, 8). These forms distribute the force over a bigger surface area there by allowing the fitting of 3D shapes. To increase rigidity the thin metal is coated with a high friction material, in the drawing a 1 mm aluminium sheet with several ramifications of 10 mm width and a coating of PU glue has been used.

Some additional advantages of this fixation are that the ramifications make the final structure more rigid and also the fixation part does not have to be detachable.

In order to keep in place this fixation between the layers of the laminated structure, one group of ramifications is inserted through slits of one layer, facilitating the insertion of the layers on the flexible envelope without limiting its own flexibility.

The orthosis shall be used as followed. The patient should first wrap the orthosis around the leg when the structure is in its soft state. The orthosis should be closed with a self gripping fastener, followed by closure of the adjustable straps (17), ensuring that the polycentric joint (20) of the orthosis is well positioned by moving his/her articulation: The structure is then made rigid by applying a vacuum inside the envelopes, using a manual self-powered electrical vacuum pump or any other vacuum source. The valve is closed and the pump pulled out. A final re-adjustment to the Velcro© and straps, and the orthosis is ready to use.

In addition to knee orthosis application described above, the present invention provides many additional applications. One of them may be incorporation into orthotic devices such as ankle foot orthosis (AFO) and insoles, or shoes. AFO is an orthosis to prevent footdrop problem caused by weakness that occurs in specific muscles of the ankle and the foot. Generally AFOs are made with plastics to support ankle instability. As the fitting element with controlled stiffness is capable of be tailored in various shapes, it enables the AFO to be completely soft and partially hard around ankle when rigidified. As such the fitting element may be employed as sock or shoe liner in shoe as well as in skating and skiing boots in order to provide well-fitting.

Protective equipment in sports, for example, knee and chest guards, helmets, wrist protections and so on, is also a potential area to which the fitting element is applicable. In these equipments, the fitting element around a body part to be protected can provide shock absorbency from external impact.

In this text, the term "comprises" and its derivations (such as "comprising", etc.) should not be understood in an excluding sense, that is, these terms should not be interpreted as excluding the possibility that what is described and defined may include further elements, steps, etc.

On the other hand, the invention is obviously not limited to the specific embodiment(s) described herein, but also encompasses any variations that may be considered by any person skilled in the art (for example, as regards the choice of materials, dimensions, components, configuration, etc.), within the general scope of the invention as defined in the claims.

The invention claimed is:

1. A body fitting element with negative pressure controlled stiffness for immobilizing an external body member, extremity or part, the body fitting dement comprising a gas tight envelope, a plurality of layers fitted in the envelope and a valve adapted to evacuate the interior of the envelope, wherein the layers comprise a core made of a textile of polyethylene terephthalate fibers and a first cover layer at both sides of the core made of a polyurethane, and wherein the body fitting element generally conforms to a part of the exterior of a body.

2. The body fitting element according to claim 1 wherein the core made of polyethylene terephthalate fibers is comprised of woven ribbons.

3. The body fitting element according to claim 2 wherein the core made of polyethylene terephthalate fibers is comprised of horizontally and vertically positioned ribbons provided with slits so as to enable interconnection of the ribbons.

4. The body fitting element according to claim 2 wherein the woven ribbons are composed of a flexible high Young's modulus textile of a width of 8 mm or less.

5. The body fitting element according to claim 1 further comprising a thin strap-shaped second covering of a material having a low friction coefficient on one side of the core and in contact with the first cover layer.

6. The body fitting element according to claim 5 wherein the thin strap-shaped second covering comprises sewing lines of thread.

7. The body fitting element according to claim 1 further comprising an air permeable layer in contact with an internal side of the envelope where the valve is placed.

8. An orthopedic device comprising a body fitting element as in any one of the previous claims in a C-shape and further comprising an elastic member connecting sides of said body fitting element so that the orthopedic device has a shape of a loop.

9. An orthopedic device comprising at least a body fitting element as in claim 1 and further comprising a thin ramified metal layer inside said body fitting element and a fixation through it accessible from outside the gas-tight envelope adapted to fix the orthopedic device to a mechanical external part.

10. Orthopedic device comprising a pair of independent body fitting elements as claimed in claim 1 and an empty chamber interposed between said pair of body fitting elements.

11. Method of fitting the orthopedic device of claim 10 comprising the steps of:
    a. applying the device to an external member, extremity or part of a body to be fitted;
    b. producing a vacuum in a first element of the pair of body fitting elements which is further away from the body;
    c. inflating the empty chamber;
    d. producing a vacuum in a second element of the pair of body fitting elements that is closer to the body;
    e. removing the vacuum in the first element and pressure in the empty chamber;
    f. applying a vacuum in the empty chamber;
    g. applying a vacuum in the first element; and
    h. immobilizing the external member, extremity or part of the body.

* * * * *